US010582892B2

(12) United States Patent
Tang et al.

(10) Patent No.: US 10,582,892 B2
(45) Date of Patent: Mar. 10, 2020

(54) BLOOD VESSEL IMAGE LOCATING SYSTEM

(71) Applicant: ZD MEDICAL (HANGZHOU) CO., LTD., Hangzhou (CN)

(72) Inventors: Lei Tang, Nanjing (CN); Ming Cai, Nanjing (CN)

(73) Assignee: ZD MEDICAL (HANGZHOU) CO., LTD., Hangzhou (CN)

(*) Notice: Subject to any disclaimer, the term of this patent is extended or adjusted under 35 U.S.C. 154(b) by 891 days.

(21) Appl. No.: 14/941,358

(22) Filed: Nov. 13, 2015

(65) Prior Publication Data
US 2016/0354030 A1 Dec. 8, 2016

Related U.S. Application Data

(63) Continuation of application No. PCT/CN2013/086094, filed on Oct. 28, 2013.

(51) Int. Cl.
A61B 5/00 (2006.01)
G06T 7/11 (2017.01)
(Continued)

(52) U.S. Cl.
CPC ............ A61B 5/489 (2013.01); A61B 5/0059 (2013.01); G06T 5/00 (2013.01); G06T 7/0012 (2013.01);
(Continued)

(58) Field of Classification Search
CPC ........ A61B 2562/0238; A61B 2576/02; A61B 5/0059; A61B 5/489; G06T 2207/20112;
(Continued)

(56) References Cited

U.S. PATENT DOCUMENTS 5,409,011 A * 4/1995 Alexeev ............ A61B 5/04282
600/546
6,230,046 B1 5/2001 Crane et al.
(Continued)

FOREIGN PATENT DOCUMENTS

WO 2013/019904 A2 2/2013

OTHER PUBLICATIONS

European Patent Office, Extended European Search Report dated Apr. 13, 2016 for EP Application No. 13884573.0.

Primary Examiner — Ruth S Smith
(74) Attorney, Agent, or Firm — Perkins Coie LLP

(57) ABSTRACT

Disclosed is a vascular image positioning system, including an image enhancing device (1) and an image projection device (2) used cooperatively with the vascular image enhancing device (1). The transmission light emitted by the enhancing device (1) passed through the sites of the human body surface to be tested, is received by the image projection device (2), and after image processing, forms in situ images at sites on the surface of the skin of the human body to be tested. The enhancing device (1) comprises a light emitting unit (101) and a drive unit (102) driving the light emitting unit (101) to emit light. The vascular image positioning system provides the function of using a transmission light source to achieve in situ imaging of the blood vessels at the sites to be tested; secondly, it also provides a mode for combining a transmission light source with a reflection light source, thereby strengthening the function of in situ imaging and widening the application range.

7 Claims, 2 Drawing Sheets

(51) Int. Cl.
*G06T 7/70* (2017.01)
*G06T 5/00* (2006.01)
*G06T 7/00* (2017.01)
*H04N 5/232* (2006.01)
*H04N 5/243* (2006.01)
*H04N 9/31* (2006.01)

(52) U.S. Cl.
CPC .................. *G06T 7/11* (2017.01); *G06T 7/70* (2017.01); *H04N 5/23241* (2013.01); *H04N 5/243* (2013.01); *H04N 9/31* (2013.01); *A61B 2562/0238* (2013.01); *A61B 2576/02* (2013.01); *G06T 2207/20112* (2013.01); *G06T 2207/20172* (2013.01); *G06T 2207/30101* (2013.01)

(58) Field of Classification Search
CPC . G06T 2207/20172; G06T 2207/30101; G06T 5/00; G06T 7/0012; G06T 7/11; G06T 7/70; H04N 5/23241; H04N 5/243; H04N 9/31

See application file for complete search history.

(56) References Cited

U.S. PATENT DOCUMENTS

| | | |
|---|---|---|
| 2006/0122515 A1 | 6/2006 | Zeman et al. |
| 2006/0173352 A1* | 8/2006 | Lilge ................... A61B 5/0091 600/476 |
| 2007/0118043 A1* | 5/2007 | Oliver ................. A61B 5/0245 600/519 |
| 2007/0158569 A1 | 7/2007 | Zeman |
| 2008/0021329 A1* | 1/2008 | Wood .................. A61B 5/0059 600/476 |
| 2011/0054282 A1* | 3/2011 | Nekoomaram ...... A61B 5/0002 600/347 |
| 2011/0112407 A1 | 5/2011 | Wood et al. |
| 2011/0125028 A1* | 5/2011 | Wood .................. A61B 5/0064 600/476 |

* cited by examiner

BLOOD VESSEL IMAGE LOCATING SYSTEM

PRIORITY CLAIM

This application is a continuation of International Application No. PCT/CN2013/086094, filed Oct. 28, 2013, which claims priority to Chinese Patent Application No. 201310173394.6, filed May 13, 2013 and Chinese Patent Application No. 201320254916.0, filed May 13, 2013, all of which are incorporated herein by reference in their entirety, including drawings.

TECHNICAL FIELD

The present disclosure relates to the field of medical equipment, to a blood vessel locating device, and in particular, to a blood vessel image locating system.

BACKGROUND OF THE INVENTION

Venipuncture is one of very common manners of helping and relieving diseases of patients for medical personnel, and tens of millions of times of venipuncture are required every day all over the world. So far, location of the venipuncture basically depends on determination by the medical personnel with naked eyes in combination with work experiences; however, for some special conditions, such as obese persons, children, persons with darker skin color, and persons who have been receiving venipuncture for a long time, some difficulties occur when venipuncture is conducted.

To solve the above technical problems, technical personnel in the art are making attempts and improvements continually, for example, by using X ray or ultrasonic wave technologies; however, the above solution causes large radiation on the human body, and is not recommended. In addition, there are related patents in the art, for example, Chinese Patent No. CN202636983 (U) (Application No. 201220325995.5) entitled "Blood Vessel Detector." The technical solution disclosed in said patent comprises an information collection box in communication connection with a mobile phone or a portable computer, said information collection box comprises an M mode processing board and a dual-channel orthogonal demodulator in communication connection with the M mode processing board, a power output end of said mobile phone or portable computer is electrically connected to the M mode processing board through a transformer, and said dual-channel orthogonal demodulator is in communication connection with a 4 MHz probe. The objective of the technical solution is to achieve accurate locating of blood vessels. However, it is mainly applicable to blood vessel locating in hemodialysis surgeries, and is not applicable to common venipuncture. A prior patent of this applicant, with the Chinese Patent No. CN202446060 (U) (Application No. 201120496584.8), discloses a blood vessel image locating device. However, said technical solution has the problem that said locating device cannot achieve the information of blood vessels in relatively deep parts. This is because hairs will cause shadow on skin when the skin is irradiated with a reflection light, and the shadow is an intense image interference source. In addition, after the excessively intense irradiation light is reflected on the skin, the light entering a sensor will cause saturation of the sensor to cause image distortion. Therefore, the brightness of a reflection light source cannot be too strong, so that the transmission capacity of the reflection light is limited, and deeper blood vessel tissue cannot be displayed. Therefore, a new locating device is in urgent need to solve the above technical problem.

Figure 1:
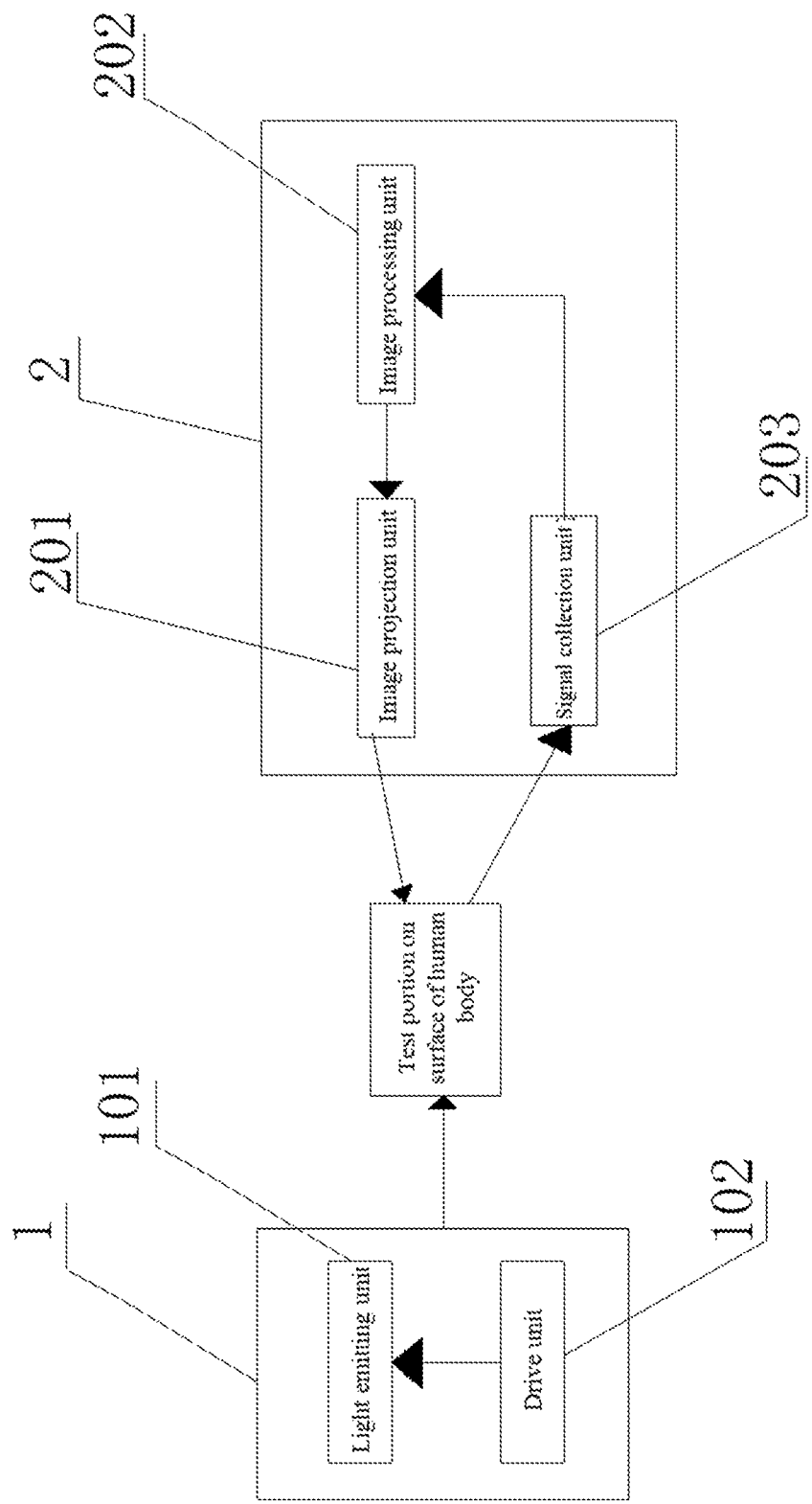
FIG. 1 is a schematic diagram of an example of the present disclosure.

In the drawings: 1. enhancing device, 2. image projection device, 101. light emitting unit, 102. drive unit, 103. brightness adjusting unit, 104. power display unit, 106. sensing switch-on circuit, 107. timing switch, 201. image projection unit, 202. image processing unit, 203. signal collection unit, 204. light emitting unit.

DETAILED DESCRIPTION OF THE INVENTION

To implement the above objectives, a technical solution of the present disclosure is described as follows: a blood vessel image locating system, characterized in that said blood vessel image locating system comprises a blood vessel image enhancing device and an image projection device for use in combination with the enhancing device, a transmission light emitted by said enhancing device penetrates through a test portion on a surface of a human body, and is received by the image projection device and subjected to image processing to provide in situ imaging on the skin surface of the test portion of the human body.

As an improvement in the present disclosure, the enhancing device comprises a light emitting unit and a drive unit driving the light emitting unit to emit light, the wavelength of the light emitted by the light emitting unit is 730 nm to 990 nm. The drive unit comprises a power supply and a drive circuit connecting the power supply and the light emitting unit. A transmission light of the above wavelength penetrates through a test portion on a surface of a human body, and is received by the image projection device to provide in situ imaging on the skin surface of the test portion of the human body, wherein the test portion is preferably irradiated with the transmission light in a vertical manner, or may also form a certain angle with the test portion.

As an improvement in the present disclosure, the enhancing device further comprises a sensing switch-on circuit for detecting whether a region adjacent to a light emission window is covered or not. The sensing switch-on circuit is mainly used to detect the covered region adjacent to the light emission window, and turns on a switch of an LED to emit light only when it detects that the region adjacent to the infrared light emission window is covered, thereby achieving a battery saving objective.

As an improvement in the present disclosure, the enhancing device further comprises a timing switch. When the enhancing device needs to be used discontinuously for a long time, the timing switch is turned on to save power and prolong the life time of the device to some extent.

As an improvement in the present disclosure, the enhancing device further comprises a brightness adjusting unit to adjust the brightness of the enhancing device as required. On one hand it can satisfy the light intensity requirements. On the other hand, it can adjust according to the blood vessel distribution condition of a patient's test portion to have a broader application scope.

As an improvement in the present disclosure, the enhancing device further comprises a power display unit for displaying the battery power, so as to monitor the battery power timely.

As an improvement in the present disclosure, the image projection device comprises a signal collection unit, an image processing unit, and an image projection unit. Said signal collection unit is used to collect a space distribution image of the transmission light or the diffuse reflection light on the test portion of the skin surface of the human body. Said image processing unit performs a signal processing on the image collected by the signal collection unit, to obtain a blood vessel image and transmit the blood vessel image to the image projection unit. Said image projection unit receives the signal from the image processing unit, and projects the blood vessel image to the test portion on the surface of the human body.

As an improvement in the present disclosure, said image projection device further comprises a light emitting unit. Said light emitting unit is used to emit exciting light to the test portion on the surface of the human body. The exciting light is mainly used to conduct diffuse reflection on the test portion of the human body, thereby further enhancing the in situ imaging technology of blood vessels, and improving the definition of the in situ imaging.

As an improvement in the present disclosure, said light emitting unit comprises at least one light emitting diode.

As an improvement in the present disclosure, said light emitting unit comprises at least two light emitting diodes, and at least two light emitting diodes of said light emitting diodes emit exciting light of different wavelengths.

As an improvement in the present disclosure, said power supply comprises a rechargeable battery, a non-rechargeable battery, or a combination thereof. Multiple charging methods are provided to provide more choices for medical personnel.

As an improvement in the present disclosure, the rechargeable battery is configured as a fixed or movable detachable structure.

Compared with the prior art, the present disclosure has the following advantages: 1) The blood vessel image locating system first provides a function of implementing in situ imaging of blood vessels of a test portion using a transmission light source, and solves the technical problems cannot be solved by reflection light imaging in the prior art. That is, said system comprises the enhancing device and the image projection device for use in combination with the enhancing device. The transmission light emitted by the enhancing device penetrates through the test portion on the surface of the human body. After the transmission light is received by the image projection device and subjected to the image processing, in situ imaging is implemented on the skin surface of the test portion of the human body. The light emitted by the enhancing device is infrared transmission light. Since the transmission light can penetrate through deep tissue of the human body, it can display blood vessel information of deeper portions. In addition, since the light irradiates from bottom to top, no shadow will be formed on the skin due to the hair on the skin surface to generate undesired image factors. For example, hair has a diffraction effect because it is relatively thin. Because hair has some light transmittance, no infrared image of the hair will be formed after the transmission light penetrates through the hair. The pure reflection light used in the prior art has the above defects. Hair can cause shadow on the skin when the skin is irradiated with a reflection light, and the shadow is an intense image interference source. In addition, an excessively intense irradiation light enters a sensor after reflected on the skin will cause saturation of the sensor to cause image distortion. Therefore, the brightness of a reflection light source cannot be too strong. Accordingly, the transmission capacity of the reflection light is limited, and deeper blood vessel tissue cannot be displayed. 2) The enhancing device further comprises a battery power display unit and a battery charging circuit for displaying the battery power. Said device is simple and convenient as it may use a battery as the power supply to supply power, or use an external power supply to supply power. 3) The enhancing device further comprises the sensing switch-on circuit unit, which is mainly used to detect the covered region adjacent to the light emission window. It turns on the switch of an LED to emit light only when it detects that the region adjacent to the infrared light emission window is covered, thereby achieving the battery saving objective. 4) The enhancing device further comprises a timing switch. When the enhancing device needs to be used discontinuously for a long time, the timing switch is turned on to save power and prolong the life time of the device to some extent. 5) The blood vessel image locating system implements a manner of combining a transmission light source and a reflection light source. That is, it uses the transmission light supplemented by the reflection light, so as to implement the in situ imaging function of blood vessels of the test portion. The transmission manner is combined with the reflection manner to greatly enhance the in situ imaging function on the skin, and achieve a broader application scope.

To deepen the understanding of the present disclosure, the present disclosure is described in detail in the following in combination with the drawings and embodiments.

Example 1

Referring to FIG. 1, a blood vessel image locating system, said blood vessel image locating system comprised a blood vessel image enhancing device 1 and an image projection device 2 for use in combination with the enhancing device 1, a transmission light emitted by said enhancing device 1 penetrated through a test portion on a surface of a human body, and was received by the image projection device 2 and subjected to image processing to provide in situ imaging on the skin surface of the test portion of the human body. The blood vessel image locating system presented colors of blood vessel portions and non-blood vessel portions clearly on the skin surface according to the skin color of the person tested.

Example 2

Referring to FIG. 1, as an improvement in the present disclosure, said enhancing device 1 comprised a light emitting unit 101 and a drive unit 102 driving the light emitting unit to emit light, the wavelength of the light emitted by the light emitting unit 101 was 730 nm to 990 nm, preferably 730-780 nm, 820-880 nm, 920-980 nm, and more preferably 760 nm, 850 nm, 960 nm, and the like. In this range, less transmission light was absorbed by human body tissues, and more transmission light penetrated through the test portion. Therefore, more information of the test portion could be gathered, and the multiple wavelengths further improved the definition of the image. Said drive unit 102 comprised a power supply and a drive circuit connecting the power supply and the light emitting unit. After a transmission light of the above wavelength penetrated through a test portion on a surface of a human body, it was received by the image projection device 2 to provide in situ imaging on the skin surface of the test portion of the human body. The test portion was preferably irradiated with the transmission light in a vertical manner, or with a certain angle with the test portion. Other structures and advantages thereof were completely the same as those of Example 1.

Example 3

Figure 2:
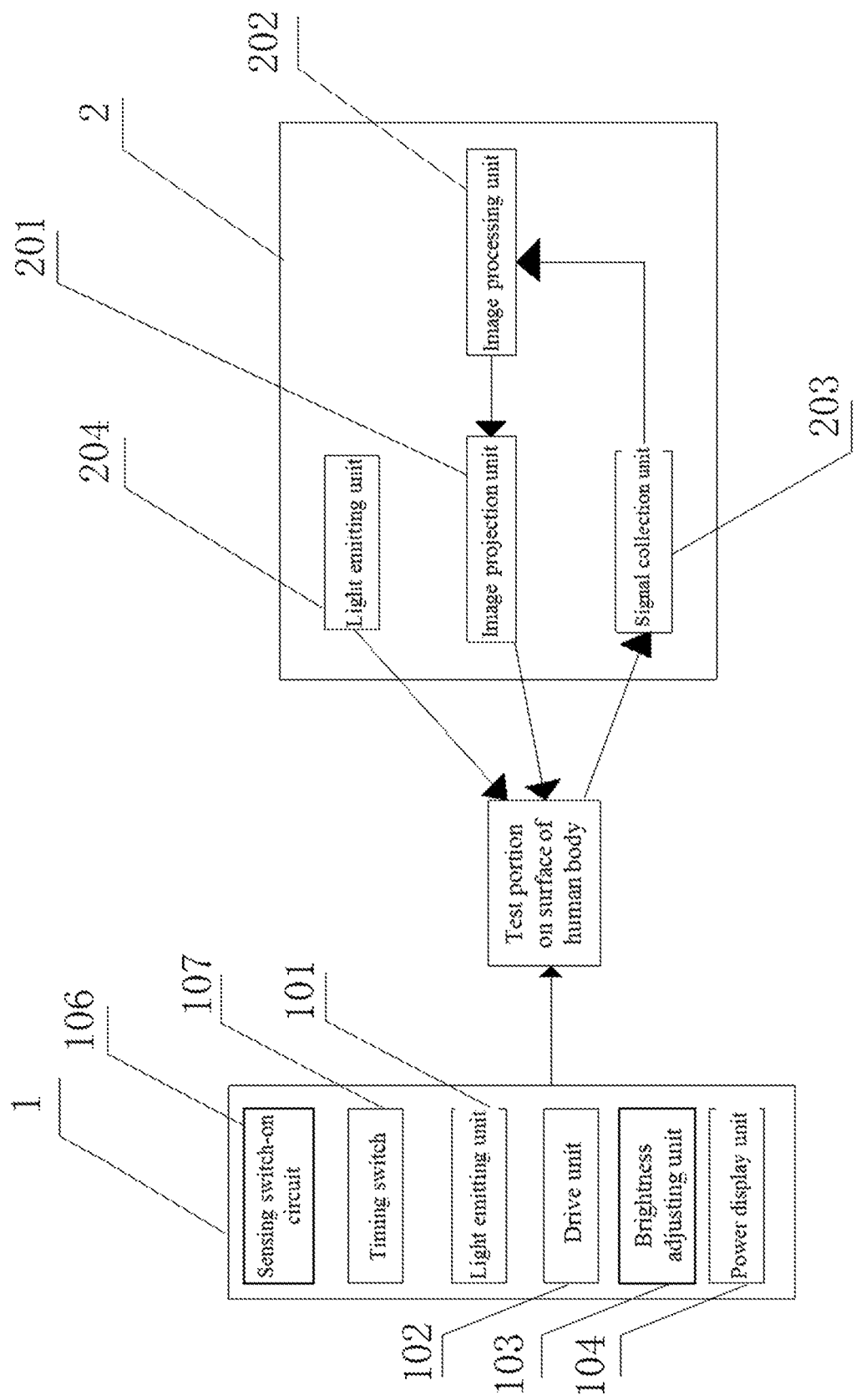
FIG. 2 is a schematic diagram of another example of the present disclosure.

Referring to FIG. 2, as an improvement in the present disclosure, the enhancing device 1 further comprised a sensing switch-on circuit 106 for detecting whether a region adjacent to a light emission window was covered. The sensing switch-on circuit was mainly used to detect the covered region adjacent to the light emission window, and turned on a switch of an LED to emit light only when it detected that the region adjacent to the infrared light emission window was covered, thereby achieving a battery saving objective. Other structures and advantages thereof were completely the same as those of Example 1.

Example 4

Referring to FIG. 2, as an improvement in the present disclosure, the enhancing device 1 further comprised a timing switch 107. When the enhancing device needed to be used discontinuously for a long time, the timing switch was turned on to save power and prolong the life time of the device to some extent. Other structures and advantages thereof were completely the same as those of Example 1.

Example 5

Referring to FIG. 2, as an improvement in the present disclosure, the enhancing 1 further comprised a brightness adjusting unit 103 to adjust the brightness of the enhancing device as required. On one hand it could fulfill the light intensity requirements. On the other hand, it could adjust according to the blood vessel distribution condition of a patient's test portion to have a broader application scope. Other structures and advantages thereof were completely the same as those of Example 1.

Example 6

Referring to FIG. 2, as an improvement in the present disclosure, the enhancing device further comprised a power display unit 104 for displaying the battery power, so as to monitor the battery power timely. Other structures and advantages thereof were completely the same as those of Example 1.

Example 7

Referring to FIG. 1, as an improvement in the present disclosure, the image projection device 2 comprised a signal collection unit 203, an image processing unit 202, and an image projection unit 201. The signal collection unit 203 collected a space distribution image of the transmission light on the test portion of the skin surface of the human body, and the collected transmission light reflected the space distribution condition of blood vessel of the test portion of the human body. The signal connecting unit 203 transmitted the collected information to the image processing unit, and the image processing unit 202 performed a signal processing on the image collected by the signal collection unit, to obtain a visible blood vessel image. The blood vessel image was transmitted to the image projection unit 201. The image projection unit 201 converted the signal into the blood vessel image, and presented the distribution condition of the blood vessel at the test portion on the surface of the human body, i.e., in situ imaging of the skin implemented using a transmission light. Other structures and advantages thereof were completely the same as those of Example 1.

Example 8

Referring to FIG. 2, as an improvement in the present disclosure, the image projection device 2 further comprised a light emitting unit 204. The light emitting unit 204 was used to emit exciting light to the test portion on the surface of the human body, and the exciting light was mainly used to conduct diffuse reflection on the test portion of the human body. In this case, the signal collection unit 203 collected both the space distribution image of the transmission light that penetrated through the test portion of the skin surface of the human body, and the space distribution image of the diffuse reflection light. The collected transmission light and diffuse reflection light reflected the space distribution condition of the blood vessel at the test portion of the human body. The signal connecting unit 203 transmitted the collected information to the image processing unit, and the image processing unit 202 performed a signal processing on the image collected by the signal collection unit, to obtain a visible blood vessel image. The blood vessel image was transmitted to the image projection unit 201. The image projection unit 201 converts the signal into the blood vessel image, and presented the distribution condition of the blood vessel at the test portion on the surface of the human body, that is, in situ imaging of the skin was implemented using the principle of combined transmission light and reflection light. The technical solution could display complicated blood vessel distribution more clearly, and had a broader application range. Other structures and advantages thereof were completely the same as those of Example 1.

Example 9

Referring to FIG. 1 or FIG. 2, as an improvement in the present disclosure, said light emitting units 101 and 204 comprised at least one light emitting diode. Other structures and advantages thereof were completely the same as those of Example 1.

Example 10

Referring to FIG. 1 or FIG. 2, as an improvement in the present disclosure, the light emitting units 101 and 204 comprised at least two light emitting diodes, and said light emitting diodes emit exciting light of at least two different wavelengths. By comparing and analyzing the signal-to-noise difference in the images collected under different wavelengths, the definition of the signal could be improved, the noise was reduced, and the image quality was optimized to provide a clearer in situ imaging of the test portion. Other structures and advantages thereof were completely the same as those of Example 1.

Example 11

As an improvement in the present disclosure, said power supply comprised a rechargeable battery, a non-rechargeable battery, or a combination thereof. Multiple charging methods were provided to provide more choices for medical personnel. Other structures and advantages thereof were completely the same as those of Example 1.

Example 12

As an improvement in the present disclosure, said rechargeable battery was configured as a fixed or movable detachable structure. The battery was configured as the movable detachable structure. Thus, when a portion was damaged, it was necessary to only replace the damaged portion without replacing the whole, which saved the cost to some extent and prolonged its service life. Other structures and advantages thereof were completely the same as those of Example 1.

The present disclosure may further combine Example 1 with at least one of the technical features described in Examples 2, 3, 4, 5, 6, 7, 8, 9, 10, 11, or 12 as needed, so as to form a new embodiment.

It should be noted that, the above examples are merely preferred embodiments of the present disclosure, and are not intended to limit the protection scope of the present disclosure. Equivalent replacement or substitution made on the basis of the above technical solution shall fall within the protection scope of the present disclosure, and the protection scope of the present disclosure is subject to the claims.

What is claimed is:

1. A blood vessel image locating system comprising: a blood vessel image enhancing device and an image projection device for use in combination with the blood vessel image enhancing device to provide an in situ imaging projection on a test portion on a surface of a human body, wherein:

the blood vessel image enhancing device and the image projection device are adapted to be positioned at opposite sides of the test portion on the surface of the human body;

the blood vessel image enhancing device emits a transmission light that penetrates through the test portion on the surface of the human body; the blood vessel image enhancing device comprises a first light emitting unit and a drive unit driving the first light emitting unit to emit the transmission light, the wavelength of the transmission light emitted by the first light emitting unit is 730 nm to 990 nm; the drive unit comprises a power supply and a drive circuit connecting the power supply and the first light emitting unit;

the image projection device comprises a second light emitting unit, wherein: the second light emitting unit is used to emit an exciting light to the test portion on the surface of the human body and generate a diffuse reflection light through diffuse reflection from the test portion on the surface of the human body; and the image projection device further comprises a signal collection unit, an image processing unit, and an image projection unit, wherein: said signal collection unit is used to collect a space distribution image of the transmission light and the diffuse reflection light on the test portion on the surface of the human body; said image processing unit performs a signal processing on the image collected by the signal collection unit, to obtain a blood vessel image and transmit the blood vessel image to the image projection unit; and said image projection unit receives the signal from the image processing unit, and projects the blood vessel image to the test portion on the surface of the human body to provide the in situ imaging.

2. The blood vessel image locating system according to claim 1, characterized in that said blood vessel image enhancing device further comprises a brightness adjusting unit.

3. The blood vessel image locating system according to claim 1, characterized in that said blood vessel image enhancing device further comprises a power display unit.

4. The blood vessel image locating system according to claim 1, characterized in that said first and second light emitting units respectively comprise at least one light emitting diode.

5. The blood vessel image locating system according to claim 1, characterized in that said first and second light emitting units respectively comprise at least two light emitting diodes, and at least two light emitting diodes of the light emitting diodes emit exciting light of different wavelengths.

6. The blood vessel image locating system according to claim 1, characterized in that said power supply comprises a rechargeable battery, a non-rechargeable battery, or a combination thereof.

7. The blood vessel image locating system according to claim 6, characterized in that said rechargeable battery is configured as a fixed or movable detachable structure.

* * * * *